(12) United States Patent
Phadke et al.

(10) Patent No.: US 10,406,108 B1
(45) Date of Patent: *Sep. 10, 2019

(54) THYROID HORMONE ORAL DOSAGE FORMS AND METHODS OF USING THE SAME

(71) Applicant: GENUS LIFESCIENCES INC., Allentown, PA (US)

(72) Inventors: Shivaji Phadke, Berkeley Heights, NJ (US); Vaishnavi Parikh, Sellersville, PA (US)

(73) Assignee: GENUS LIFESCIENCES INC., Allentown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/257,755

(22) Filed: Jan. 25, 2019

Related U.S. Application Data

(63) Continuation of application No. 15/934,185, filed on Mar. 23, 2018, now Pat. No. 10,231,931.

(51) Int. Cl.
*A61K 9/20* (2006.01)
*A61K 31/198* (2006.01)

(52) U.S. Cl.
CPC .......... *A61K 9/2054* (2013.01); *A61K 9/2013* (2013.01); *A61K 9/2031* (2013.01); *A61K 9/2095* (2013.01); *A61K 31/198* (2013.01)

(58) Field of Classification Search
None
See application file for complete search history.

(56) References Cited

U.S. PATENT DOCUMENTS

| | | | |
|---|---|---|---|
| 5,225,204 A | 7/1993 | Chen et al. | |
| 5,635,209 A | 6/1997 | Groenewoud et al. | |
| 5,753,254 A | 5/1998 | Khan et al. | |
| 5,955,105 A | 9/1999 | Mitra et al. | |
| 5,958,979 A | 9/1999 | Lahr et al. | |
| 6,056,975 A | 5/2000 | Mitra et al. | |
| 6,399,101 B1 | 6/2002 | Frontanes et al. | |
| 6,555,581 B1 | 4/2003 | Franz et al. | |
| 6,569,463 B2 | 5/2003 | Patel et al. | |
| 6,645,526 B2 | 11/2003 | Hanshew, Jr. et al. | |
| 6,855,333 B1 | 2/2005 | Spireas | |
| 6,923,988 B2 | 8/2005 | Patel et al. | |
| 6,936,274 B2 | 8/2005 | Hanshew, Jr. et al. | |
| 7,052,717 B2 | 5/2006 | Hanshew, Jr. et al. | |
| 7,067,148 B2 | 6/2006 | Franz et al. | |
| 7,101,569 B2 | 9/2006 | Franz et al. | |
| 7,195,779 B2 | 3/2007 | Hanshew, Jr. et al. | |
| 8,293,272 B2 | 10/2012 | Burghart et al. | |
| 8,779,000 B1 | 7/2014 | Parikh et al. | |
| 9,006,289 B2 | 4/2015 | Jiang et al. | |
| 9,271,951 B2 | 3/2016 | Kirsch et al. | |
| 9,682,045 B2 | 6/2017 | Kannan et al. | |
| 10,231,931 B1 | 3/2019 | Phadke et al. | |
| 2009/0297566 A1* | 12/2009 | Brinkman | A61K 31/198 424/400 |
| 2015/0025148 A1* | 1/2015 | Parikh | A61K 31/198 514/567 |
| 2016/0331711 A1 | 11/2016 | Parikh et al. | |

OTHER PUBLICATIONS

FDA Acts to Ensure Thyroid Drugs Don't Lose Potency Before Expiration Date, FDA Press Release, Oct. 3, 2007, 1 page.
Zhang et al., "Development of Oral Fast-Disintegrating Levothyroxine Films for Management of Hypothyroid in Pediatrics", Tropical Journal of Pharmaceutical Research, Oct. 2015, 14(10), pp. 1755-1762.

* cited by examiner

*Primary Examiner* — Susan T Tran
*Assistant Examiner* — William Craigo
(74) *Attorney, Agent, or Firm* — K&L Gates LLP (57) ABSTRACT

Novel thyroid hormone oral dosage forms and methods of making and using the thyroid hormone oral dosage forms are disclosed.

11 Claims, 5 Drawing Sheets

SECTION "B" - "B"

FIG. 4B

| | 25 µg | 50 µg | 75 µg | 88 µg | 100 µg | 112 µg | 125 µg | 137 µg | 150 µg | 175 µg | 200 µg | 300 µg |
|---|---|---|---|---|---|---|---|---|---|---|---|---|
| Levothyroxine Sodium | 0.025 | 0.05 | 0.075 | 0.088 | 0.1 | 0.112 | 0.125 | 0.137 | 0.150 | 0.175 | 0.200 | 0.300 |
| Avicel HFE 102, | 110.425 | 110.500 | 109.890 | 110.230 | 110.230 | 110.290 | 110.292 | 110.280 | 110.140 | 110.430 | 110.200 | 110.190 |
| Mannitol | 14.65 | 14.65 | 14.65 | 14.65 | 14.65 | 14.65 | 14.65 | 14.65 | 14.65 | 14.43 | 14.65 | 14.65 |
| HPMC K100 LV CR LH | 3 | 3 | 3 | 3 | 3 | 3 | 3 | 3 | 3 | 3 | 3 | 3 |
| BHA | 0.3 | 0.3 | 0.3 | 0.3 | 0.3 | 0.3 | 0.3 | 0.3 | 0.3 | 0.3 | 0.3 | 0.3 |
| Talc | 1.00 | 1.00 | 1.00 | 1.00 | 1.00 | 1.00 | 1.00 | 1.00 | 1.00 | 1.00 | 1.00 | 1.00 |
| Magnesium Stearate | 0.5 | 0.5 | 0.5 | 0.5 | 0.5 | 0.5 | 0.5 | 0.5 | 0.5 | 0.5 | 0.5 | 0.5 |
| FD&C Yellow # 6 Aluminium Lake 17-19% | 0.1 | 0 | 0 | 0.0325 | 0.02 | 0 | 0.0702 | 0 | 0 | 0 | 0 | 0.005 |
| FD&C Blue # 1 Aluminium Lake 11-13% | 0 | 0 | 0 | 0.065 | 0 | 0 | 0.0273 | 0.13 | 0 | 0.0572 | 0 | 0.033 |
| D&C Yellow # 10 Aluminium Lake 14-18% | 0 | 0 | 0 | 0.13 | 0.2 | 0 | 0 | 0 | 0 | 0 | 0 | 0.022 |
| FD&C Red # 40 Aluminium Lake 14-16% | 0 | 0 | 0.26 | 0 | 0 | 0 | 0.0351 | 0 | 0 | 0 | 0.15 | 0 |
| FD&C Blue # 2 Aluminium Lake 12-14% | 0 | 0 | 0.325 | 0 | 0 | 0.13 | 0 | 0 | 0.26 | 0 | 0 | 0 |
| D&C Red # 27 Aluminium Lake | 0 | 0 | 0 | 0 | 0 | 0.0195 | 0 | 0 | 0 | 0.052 | 0 | 0 |
| D&C Red # 30 Aluminium Lake | 0 | 0 | 0 | 0 | 0 | 0 | 0 | 0 | 0 | 0.052 | 0 | 0 |

FIG. 5

THYROID HORMONE ORAL DOSAGE FORMS AND METHODS OF USING THE SAME

CROSS-REFERENCE TO RELATED APPLICATION

This application is a continuation application claiming priority under 35 U.S.C. § 120 to U.S. patent application Ser. No. 15/934,185, filed Mar. 23, 2018, entitled THYROID HORMONE ORAL DOSAGE FORMS AND METHODS OF USING THE SAME, the entire disclosure of which is hereby incorporated herein by reference in its entirety.

FIELD OF THE TECHNOLOGY

The present disclosure relates to thyroid hormone oral dosage forms and to methods of making and storing thyroid hormone oral dosage forms.

DESCRIPTION OF THE BACKGROUND OF THE TECHNOLOGY

Hypothyroidism is a common endocrine disorder characterized by a deficiency of thyroid hormone. Worldwide, iodine deficiency is the major cause of hypothyroidism. In the United States and other areas in which iodine intake is adequate, autoimmune thyroid disease (Hashimoto's disease) is the most common cause of hypothyroidism. Hypothyroidism may also be drug-induced or otherwise iatrogenic.

Hypothyroidism usually is a primary process in which the thyroid gland is unable to produce sufficient amounts of thyroid hormone. Hypothyroidism can also be a secondary process in which the thyroid gland is normal but receives insufficient stimulation because of low secretion of thyrotropin (i.e., thyroid-stimulating hormone or "TSH") by the pituitary gland. Also, in tertiary hypothyroidism the hypothalamus releases inadequate levels of thyrotropin-releasing hormone (TRH), which leads to insufficient release of TSH, and in turn causes inadequate thyroid stimulation.

Thyroid hormone deficiency has a wide range of effects. Systemic effects result from either derangements in metabolic processes or directly by myxedematous infiltration (i.e., accumulation of glucosaminoglycans in the tissues). Hypothyroid changes in the heart result in decreased contractility, cardiac enlargement, pericardial effusion, decreased pulse, and decreased cardiac output. In the gastrointestinal tract, achlorhydria and prolonged intestinal transit time with gastric stasis can occur. Delayed puberty, anovulation, menstrual irregularities, and infertility are common. Decreased thyroid hormone also can cause increased levels of total cholesterol and low-density lipoprotein (LDL) cholesterol and a possible change in high-density lipoprotein (HDL) cholesterol because of a change in metabolic clearance. In addition, hypothyroidism may result in an increase in insulin resistance.

Third-generation TSH assays are readily available and are generally the most sensitive screening tool for primary hypothyroidism. The generally accepted reference range for normal serum TSH is 0.40-4.2 mIU/L. If TSH levels are above the reference range, the next step is to measure free thyroxine (T4). Subclinical hypothyroidism, also referred to as mild hypothyroidism, is defined as normal serum levels of free T4 and triiodothyronine (T3) with a slightly high serum TSH concentration.

Daily administration of thyroid hormone drugs is the standard treatment for hypothyroidism in humans and other mammals. An oral medication such as levothyroxine or a levothyroxine salt can restore adequate hormone levels, reversing the symptoms of hypothyroidism. In general, hypothyroidism can be adequately treated with a constant daily dose of levothyroxine (LT4). The typical human daily dosage of a levothyroxine drug is low, ranging from 25 to 300 μg. The treatment goals for hypothyroidism are to reverse clinical progression and correct metabolic derangements, as evidenced by normal blood levels of TSH and T4.

Careful dosing of levothyroxine drugs is critical to avoid over and under treatment. Symptoms of overtreatment can include, for example, tachycardia, palpitations, atrial fibrillation, nervousness, tiredness, headache, increased excitability, sleeplessness, tremors, and possible angina. Dosage resulting in under treatment of patients can result in, for example, fatigue, cold intolerance, dry skin, hair loss, muscle pain, joint pain, weakness in the extremities, mental impairment, decreased perspiration, paresthesia and nerve entrapment syndromes, blurred vision, and hearing impairment.

Thyroid hormone replacement commonly is started at anticipated full replacement dosage level in young and otherwise healthy patients. In elderly patients and those with known ischemic heart disease, treatment often begins with one-quarter to one-half anticipated full replacement dosage, and dosage is adjusted upwardly in small increments after no less than 4 to 6 weeks. For most cases of mild to moderate hypothyroidism, a starting levothyroxine dosage is 50-75 μg/day.

All thyroid hormone preparations, natural or synthetic, are intended to replace a patient's natural thyroid hormone. A normal human thyroid gland releases primarily tetraiodothyronine (levothyroxine or LT4), which is then converted to triiodothyronine (liothyronine or T3) in the target tissues. T3 is the actual active thyroid hormone. The thyroid gland forms LT4 (containing four iodine atoms) by coupling two molecules of diiodotyrosine (DIT). T3 (containing three iodine atoms) is also formed in the thyroid gland by coupling one molecule of DIT with one molecule of monoiodotyrosine (MIT). The thyroid gland stores both T4 and T3 in the thyroid colloid as thyroglobulin.

Synthetic thyroid hormone preparations are commercially available for both T3 and T4 forms of thyroid hormone. For example, liothyronine is a synthetic version of the T3 thyroid hormone triiodothyronine available as CYTOMEL® tablets from King Pharmaceuticals, St. Louis, Mo. Levothyroxine (T4) sodium is available in several commercial products including LEVOXYL® tablets (King Pharmaceuticals), UNITHROID® tablets (Jerome Stevens Pharmaceuticals, Bohemia, N.Y.), and SYNTHROID® tablets (AbbVie, Chicago, Ill.). Levothyroxine (T4) sodium is also available in a veterinary preparation known as SOLOXINE® (King Pharmaceuticals).

Levothyroxine is relatively unstable and degrades over time. For example, levothyroxine sodium is sensitive to irradiation, hydrolysis, oxidation, and heat. Degradation of the active ingredients in thyroxine dosage forms can lead to loss of potency, resulting in inadequate dosage delivery and under treatment of hypothyroidism. Some drug manufacturers have resorted to including an excess of the active ingredient in thyroxine dosage forms in anticipation of some degree of storage degradation. This practice can complicate accurate dosing and present the possibility of over dosing. Accordingly, storage stability of levothyroxine drugs is highly desirable to ensure accurate patient dosing and avoid the complications associated with under or over treatment.

U.S. Pat. No. 5,225,204 is directed to improving the stability of levothyroxine sodium and generally recites stable compositions with a complex of hydrated levothyroxine sodium and a cellulose compound, polyvinylpyrrolidone or a poloxamer where the complex is absorbed onto a cellulose carrier. The patentees provide several exemplary compositions, yet fail to provide stability information for any of the claimed compositions. In one embodiment the patent discloses the preparation of stabilized levothyroxine sodium in a dry state by mixing levothyroxine sodium with a cellulose tableting agent using geometric dilution and subsequently combining this mixture with the same or a second cellulose tableting agent, such as microcrystalline cellulose.

U.S. Pat. No. 5,635,209 generally recites a stabilized composition of levothyroxine sodium with potassium iodide and microcrystalline cellulose. The patentees provide results from a three-month accelerated stability test, but do not identify whether desiccants were used.

U.S. Pat. No. 5,753,254 relates to a solid fast dispersing dosage form wherein the therapeutic agents include thyroid hormones. This formulation is intended to be fast dissolving and stability issues are not discussed.

U.S. Pat. No. 5,955,105 generally recites stabilized hormone compositions with a water soluble glucose polymer and a cellulose polymer, and U.S. Pat. No. 6,056,975 generally recites stabilized hormone compositions with a carbohydrate with a molecular mass greater than 500 and glycine, and compositions with a reduced carbohydrate, a water soluble polysaccharide, or galactose. The patentees state that certain carbohydrates are compatible with levothyroxine, whereas others are not. The inventors include maltodextrins and cyclodextrins as a type of polysaccharide suitable for the claimed invention. The patentees provide several exemplary compositions, including the compositions of U.S. Pat. No. 5,225,204 and provide stability data for select formulations stored with and without desiccant. Some formulations were apparently more stable with a desiccant and other formulations were not. The patentees concluded that the stability of the formulations disclosed in U.S. Pat. No. 5,225,204 were "substantially worse than commercial products which were commercially available at the time the application which matured into U.S. Pat. No. 5,225,204 was filed."

U.S. Pat. No. 5,958,979 generally recites stabilizing thyroid hormone compositions with sodium thiosulfate. The patentees state that the stability of thyroid hormones is surprisingly increased with sodium thiosulfate, an antagonist in case of cyanide intoxication, when compared to conventional preparations. Exemplary compositions were packaged in commercial blister packs for stability testing. The patentees used a variety of temperatures and relative humidity values, but did not disclose the use of desiccants with the blister packs. Further, the use of substances like sodium thiosulfate in pharmaceutical preparations is undesirable from the toxicological point of view.

U.S. Pat. No. 6,399,101 generally recites pharmaceutical preparations of thyroid hormones and processes of making the same via direct compression. The patentees state that stability problems known in the art may be remedied by the use of silicified microcrystalline dioxide. The patentees hypothesize that the silicified microcrystalline cellulose creates a stabilizing matrix that protects levothyroxine particles. The stability of exemplary formulations is reported as up to 93.3% after three months of accelerated storage conditions.

U.S. Pat. No. 6,555,581 generally recites stabilized immediate release compositions with Beta-sheet form microcrystalline cellulose. The inventors of U.S. Pat. No. 6,555,581 state that "the use of the BETA-sheet microcrystalline cellulose in the compositions of the present invention substantially increases the stability of the thyroid hormone drugs, so that the patient obtains consistent potency over an extended shelf life, compared to prior thyroid hormone drugs." The inventors also note that certain earlier references, e.g., U.S. Pat. No. 5,225,204, disclosed the use of microcrystalline cellulose; however, the microcrystalline cellulose was an alpha-helix spherical microcrystalline cellulose product instead of the beta-sheet form. Further, the compositions lose up to 0.3% potency per month during an 18 month stability period.

U.S. Pat. No. 6,569,463 generally recites pharmaceutical delivery systems that contain a substrate and an encapsulation coat. U.S. Pat. No. 6,569,463 contains a broad disclosure of active ingredients that may be used in the delivery system, including hydrophobic active ingredients. L-thyroxine is disclosed in a non-limiting list of examples of hydrophobic active ingredients. The patentees do not disclose stability data, and do not provide examples of a levothyroxine composition.

U.S. Pat. Nos. 6,645,526, 6,936,274, and 7,195,779 generally recite stabilized compositions with thyroxine, an alditol, and saccharide. The patentees state that despite an understanding that certain excipients contribute to the instability of levothyroxine, they identified a stable composition with levothyroxine and carbohydrate, monosaccharide, or disaccharide excipient. The patentees hypothesized that mixing the alditol and saccharide at an early stage of manufacture provided the stability for the formulation. The patentees disclose stability data for storage up to only 5 days at ambient humidity, and do not disclose the use of desiccants.

U.S. Pat. No. 6,855,333 generally recites low compression forms of stabilized thyroid drug compositions. The patentees identify levothyroxine as a drug that rapidly degrades in the presence of light, under conditions of high temperature, or in the presence of certain excipients, including carbohydrates and certain dyes. The patentees describe embodiments where a drug substance is pretreated with a non-volatile, water-immiscible liquid to protect the drug from environmental or equilibrium moisture. The patentees further state that a high degree of tablet compression contributes to moisture-induced degradation. The patentees included tables with stability data for several exemplary compositions when stored at 60° C. and 75% relative humidity for 5 days, and do not disclose the use of desiccants.

U.S. Pat. No. 6,923,988 generally recites pharmaceutical delivery systems in the form of a solid carrier. U.S. Pat. No. 6,923,988 contains a broad disclosure of active ingredients that may be used in the delivery system, including hydrophobic active ingredients. L-thyroxine is disclosed in a non-limiting list of examples of hydrophobic active ingredients. The patentees do not disclose stability data, and do not provide examples of a levothyroxine composition.

U.S. Pat. No. 7,052,717 generally recites stabilized compositions with thyroxine and an antioxidant. The patentees state that the recited composition with thyroxine active drug substance, an alditol, and a monosaccharide or disaccharide provide a synergistic increase of stability. The patentees included a figure with stability data for several exemplary compositions when stored at various conditions for 5 days, and do not disclose the use of desiccants.

U.S. Pat. No. 7,067,148 generally recites stabilized thyroid hormone compositions with BETA-sheet microcrystalline cellulose. The patentees provide stability data for exemplary compositions with ALPHA-form and BETA-form microcrystalline cellulose, and when stored at 25° C. the patentees report that formulations with BETA-sheet microcrystalline cellulose were more stable than the compositions with ALPHA-form microcrystalline cellulose. The patentees do not report on the relative humidity or whether desiccants were used during storage.

U.S. Pat. No. 7,101,569 generally discloses formulations for various strengths of Levoxyl, which apparently at the time of the application contained BETA-sheet microcrystalline cellulose. The patent also contains other examples reflecting summaries of information prepared for the U.S. Food and Drug Administration. The patentees do not report on the relative humidity or whether desiccants were used during storage.

U.S. Pat. No. 8,293,272 generally discloses levothyroxine compositions with certain water activity levels below 0.4 and preferably between 0.1 and 0.3. The patentees state that removing one mol of water, and removing hygroscopic adjuvants substantially increases the stability of the composition. The patentees report on results obtained from compositions with varying water activity levels on composition stored in PVC blisters.

U.S. Pat. No. 8,779,000 generally discloses a levothyroxine sodium composition with several excipients that is free of added saccharide. In one embodiment, the formulations are made by wet granulation. The patentees do not report whether desiccants were used during storage.

U.S. Pat. No. 9,006,289 generally discloses lyophilized levothyroxine compositions with less mannitol than convention compositions. The patentees state that the disclosed composition exhibits a surprising and expected improvement in levothyroxine stability. The patentees do not report on the relative humidity or whether desiccants were used during storage.

U.S. Pat. No. 9,271,951 generally recites levothyroxine formulations with acacia and certain antioxidants. The patentees hypothesize that acacia and a certain antioxidant provide a stabilizing effect. The patentees make several compositions via wet granulation and report on the stability at 40° C. at 75% RH for up to 24 weeks. Exemplary compositions included acacia and compositions with propyl gallate exhibited greater stability than compositions with butylated hydroxyanisol, and the patentees did not identify whether desiccants were used for storage.

U.S. Patent Publication No. 2016/0331711 generally discloses compositions with levothyroxine sodium, an antioxidant, a saccharide and at least two other excipients. The patentees state that the composition has unexpectedly excellent storage-stability properties, and the active drug is surprisingly maintained at a predictable level for a substantial period of time. The patentees provide five day stability data but do not provide guidance relating to container closure systems or desiccants used therein.

U.S. Pat. No. 9,682,045 describes a stable pharmaceutical composition comprising levothyroxine sodium, one or more carbohydrates selected from the group consisting of isomalt, arabinose, dextrose, sucrose, fructose, maltose, and trehalose, and one or more pharmaceutically acceptable excipients, wherein the composition retains at least 95% of the potency of levothyroxine sodium after storage for 24 months at 25° and 75% relative humidity.

Levothyroxine tablets are available in extremely low, microgram-level dosages (e.g., 25 µg, 50 µg, 75 µg, 88 µg, 100 µg, 112 µg, 125 µg, 137 µg, 150 µg, 175 µg, 200 µg, and 300 µg). To facilitate accurate administration, commercially available tablets typically include a break-line allowing one to break tablets into two substantially equal halves. The possibility that a patient will utilize break-lines and administer only half of a tablet daily enhances the need for uniform distribution of active ingredients in tablets to avoid incorrect dosage and related complications.

Accordingly, there is a need for a thyroid hormone replacement dosage form including providing acceptable bioavailability and potency, advantageous stability, improved shelf life, and uniform distribution of active ingredients.

SUMMARY

It is understood that the inventions disclosed and described in this specification are not limited to the embodiments described in this Summary.

A non-limiting aspect of the present disclosure is directed to an immediate release oral dosage form prepared by a dry blending process and comprising a thyroid hormone or a pharmaceutically acceptable thyroid hormone salt, a hydrophilic polymer, and an antioxidant. The hydrophilic polymer may be selected from the group consisting of hydroxypropyl methylcellulose (HPMC), hydroxypropylcellulose (HPC), polyethylene oxide (PEO), or a combination of two or more of those polymers. The antioxidant of the oral dosage form may be selected from the group consisting of butylated hydroxyanisole, butylated hydroxytoluene, ethylenediaminetetraacetic acid (EDTA), and sodium metabisulfite. In certain embodiments, the oral dosage form includes levothyroxine or levothyroxine sodium. The oral dosage form exhibits advantageous stability, retaining at least 95% of an initial amount of thyroid hormone salt after storage for a predetermined time period at a temperature ranging from about 23° C. to about 27° C. and a relative humidity ranging from about 55% to about 65%. In another embodiment, the oral dosage form retains at least 95% of an initial amount of thyroid hormone salt after storage for at least about one month at a temperature ranging from about 38° C. to about 42° C. and a relative humidity ranging from about 70% to about 80%.

A non-limiting aspect of the present disclosure is directed to an immediate release oral solid dosage form prepared by a dry blending process and comprising a thyroid hormone or a pharmaceutically acceptable thyroid hormone salt and a hydrophilic polymer. In certain embodiments, when about 90 to about 100 of the oral solid dosage forms and at least about 6 grams of desiccant are placed in a container of about 55 cm$^3$ to about 125 cm$^3$ sealed with a closure, each oral solid dosage form retains at least 95% of an initial amount of the thyroid hormone or thyroid hormone salt when stored at a temperature ranging from about 23° C. to about 27° C. and a relative humidity ranging from about 55% to about 65% for six months. In certain embodiments, when the about 90 to about 100 oral solid dosage forms and the at least about 6 grams of desiccant are placed in the container of about 55 cm$^3$ to about 125 cm$^3$ each oral solid dosage form retains at least 95% of an initial amount of the thyroid hormone or thyroid hormone salt when stored at a temperature ranging from about 38° C. to about 42° C. and a relative humidity ranging from about 70% to about 80% for at least about one month.

A non-limiting aspect of the present disclosure is directed to an immediate release oral solid dosage form prepared by a dry blending process and comprising a thyroid hormone or a pharmaceutically acceptable thyroid hormone salt and a hydrophilic polymer. In certain embodiments, when about 900 to about 1000 of the oral solid dosage forms and at least about 16 grams of desiccant are placed in a container of about 225 cm$^3$ to about 360 cm$^3$ sealed with a closure, each oral solid dosage form retains at least 95% of an initial amount of the thyroid hormone or thyroid hormone salt when stored at a temperature ranging from about 23° C. to about 27° C. and a relative humidity ranging from about 55% to about 65% for six months.

A non-limiting aspect of the present disclosure is directed to a container having a volume of 55 cm$^3$ to 125 cm$^3$ containing at least one silica gel desiccant canister and about 90 to about 100 tablets or capsules of an immediate release oral dosage form including a thyroid hormone salt, and a closure sealing the container.

A non-limiting aspect of the present disclosure is directed to a container having a volume of 225 to 360 cm$^3$ containing at least one silica gel desiccant canister and about 900 to about 1000 tablets or capsules of an immediate release oral dosage form including a thyroid hormone salt, and a closure sealing the container.

A non-limiting aspect of the present disclosure is directed to a method of providing a thyroid hormone salt to a patient in need thereof, the method comprising administering an immediate release oral dosage form including a thyroid hormone salt according to the present disclosure to the patient. In another embodiment, the method includes administering the oral dosage form such that about 25 µg, 50 µg, 75 µg, 88 µg, 100 µg, 112 µg, 125 µg, 137 µg, 150 µg, 175 µg, 200 µg, or 300 µg of levothyroxine is administered to the patient in need thereof.

BRIEF DESCRIPTION OF THE DRAWINGS

Various features and characteristics of non-limiting and non-exhaustive embodiments disclosed and described in this specification may be better understood by reference to the accompanying figures, in which:

FIGS. 4A and 4B are views of a container closure system that can be used in conjunction with the container shown in FIG. 3, wherein FIG. 4A is an exterior top view of a ribbed, threaded closure cap, and FIG. 4B is a side sectional view of the cap shown in FIG. 4A.

The reader will appreciate the foregoing details, as well as others, upon considering the following detailed description of various non-limiting and non-exhaustive embodiments according to the present disclosure.

DETAILED DESCRIPTION OF CERTAIN NON-LIMITING EMBODIMENTS

Various embodiments are described and illustrated in this specification to provide an overall understanding of the disclosed compositions and methods. It is understood that the various embodiments described and illustrated in this specification are non-limiting and non-exhaustive. Thus, the present invention is not limited by the description of the various non-limiting and non-exhaustive embodiments disclosed in this specification. Rather, the invention is defined solely by the claims. Certain features and characteristics illustrated and/or described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Further, Applicant reserves the right to amend the claims to affirmatively disclaim features or characteristics that may be found present in the prior art. The various embodiments disclosed and described in this specification can comprise, consist of, or consist essentially of the features and characteristics as variously described herein.

All percentages and ratios provided herein are weight percentages based on the total weight of the respective composition, tablet, mixture, etc., unless otherwise indicated.

Any numerical ranges recited in this specification are intended to include all sub-ranges of the same numerical precision subsumed within the recited range. For example, a range of "1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this specification is intended to include all lower numerical limitations subsumed therein and any minimum numerical limitation recited in this specification is intended to include all higher numerical limitations subsumed therein. Applicant reserves the right to amend this specification, including the claims, to expressly recite any sub-range subsumed within the ranges expressly recited herein.

Disclosed herein are storage stable, immediate release thyroid hormone replacement oral dosage forms prepared by a dry blending process and comprising a thyroid hormone or a pharmaceutically acceptable salt thereof. Certain embodiments of the oral dosage form include levothyroxine sodium.

The present inventors observed that thyroid hormone replacement oral dosage forms according to the present disclosure exhibit unexpected advantageous stability. As discussed herein, the present inventors believe that the advantageous stability exhibited by oral dosage forms according to the present disclosure may result from formulating, manufacturing, packaging and storing the oral dosage form in a particular manner. Although the following description and examples refer to compositions and dosage forms including levothyroxine and/or a pharmaceutically acceptable levothyroxine salt, it to be understood that the methods and dosage forms herein may utilize other thyroid hormone compounds having the following general formula:

wherein:
$R_1$ and $R_3$ may be the same or different and are selected from acid, acyl, alcohol, alkenyl, alkyl, alkynyl, amide, aryl, cycloalkyl, hydrogen, halogen, heterocycloalkyl, ester, and ether;
$R_2$ is:

and;
$R_4$ and $R_5$ may be the same or different and are selected from acid, acyl, alcohol, alkenyl, alkyl, alkynyl, amide, aryl, cycloalkyl, heterocycloalkyl, ester, ether, halogen, and hydrogen. Levothyroxine (also known as thyroxine and L-thyroxine) and liothyronine (also known as (S)-triiodothyronine), shown below, are examples of thyroid hormones having the above chemical formula. Both levothyroxine and liothyronine can be in the form of a hydrate, a free acid, a free base, an organic salt, or an inorganic salt, and all such forms may be used in the dosage forms according to the present disclosure.

In certain embodiments according to the present disclosure, an immediate release oral dosage form prepared by a dry uniform blending process comprises a levothyroxine sodium or another thyroid hormone salt, a hydrophilic polymer, and an antioxidant, and the dosage form retains at least 95% of an initial amount of the thyroid hormone salt when stored at about six months under standard testing conditions (25° C.±2° C. and 60%±5% relative humidity), intermediate testing conditions (30° C.±2° C. and 65%±5% relative humidity), and accelerated testing conditions (40° C.±2° C. and 75%±5% relative humidity).

The dry uniform blending of the ingredients for the oral dosage form can be performed using any suitable technique known in the art, such as blending, mixing, sieving, co-milling, grinding, granulation, power granulation, or combinations of two or more of these techniques.

In one embodiment, the oral dosage is a solid form, such as for example, tablets, capsules, powders, granules, lozenges, beads, microspheres, or pellets.

In one embodiment, the oral dosage form is stored in a container having an internal volume of 55 $cm^3$ to 125 $cm^3$ including therein about 90 to about 100 oral dosage forms and at least one silica gel desiccant canister containing, for example, about 2 grams of desiccant. In certain embodiments, the oral dosage form can be stored in a 55 $cm^3$ to 125 $cm^3$ container containing between 90 and 100 oral dosage forms including at least three silica gel desiccant canisters (each canister containing, for example, about 2 grams of desiccant).

In one embodiment, the oral dosage form is stored in a container having an internal volume of 225 $cm^3$ to 360 $cm^3$ including therein about 90 to about 100 oral dosage forms and at least one silica gel desiccant canister containing, for example, about 2 grams of desiccant.

The oral dosage form can be stored in a container formed of a suitable resin. For example, the container can be made of polypropylene or a high density polyethylene. In certain embodiments, the oral dosage forms can be stored in a container that is purged with an inert gas to replace environmental oxygen prior to closure. In certain embodiments the inert gas can include nitrogen, argon, or a mixture of nitrogen and argon. In another embodiment, air space may be displaced with an inert pill packing material, for example, rayon or cotton.

In certain embodiments, the thyroid hormone salt in the oral dosage form is levothyroxine. In one embodiment, the thyroid hormone can be a hormone salt such as levothyroxine salt, liothyronine salt, or a combination of levothyroxine and liothyronine salts.

The oral dosage form may be used for any convenient dosage amount of the thyroid hormone or thyroid hormone salt. In general, the concentration of the thyroid hormone may be increased or decreased according to the judgment of the physician, pharmacist, pharmaceutical scientist, or other health care professional. In a preferred embodiment, the oral dosage form comprises levothyroxine sodium in a therapeutically effective amount or dose.

The concentration or dose of thyroid hormone/salt in the oral dosage form can vary depending on the indicated dosage. The indicated therapeutic dose of thyroid hormone salt can depend on the age and health of the patient, the severity of the condition treated, the other medications that the patient is currently taking, as well as the preference of the healthcare practitioner. Non-limiting examples of the dose of thyroid hormone salt in a 130 mg tablet or other oral dosage form according to the present disclosure can range from about 1 µg to about 400 µg, from about 1 µg to about 250 µg, from about 10 µg to about 325 µg from about 20 µg to about 150 µg, from about 30 µg to about 350 µg, from about 50 µg to about 400 µg, or from about 75 µg to about 500 µg.

The concentration of thyroid salt per oral dosage form (e.g., tablet) according to the present disclosure can range from about 0.01% to about 2%, about 0.05% to about 1%, about 0.1% to about 1%, about 0.15% to about 0.75%, or from about 0.2% to about 0.5%, by weight of the oral dosage form.

The hydrophilic polymer included in the oral dosage form according to the present disclosure is selected from, but is not limited to, at least one of hydroxypropyl methylcellulose (HPMC), hydroxypropylcellulose (HPC), polyethylene oxide (PEO), methyl cellulose, starch, polyvinylpyrrolidone (PVP), gelatin, alginate, gum arabic, polyvinyl alcohol, tragacanth, sodium alginate, microcrystalline cellulose, hydroxyethylcellulose (HEC), other cellulose polymers, sodium carboxymethylcellulose (Na-CMC), xanthan gum, carrageenan, ceratonia, chitosan, guar gum, pectin, cross-linked high amylose starch, polyethylene oxide, and combinations of two or more thereof.

In certain embodiments, the hydrophilic polymer of the immediate release oral dosage form includes the controlled release agent HPMC (hydroxypropyl methylcellulose) K100 LV CR LH (low hydroxypropyl). As is understood by those having ordinary skill, the alpha and numeric identifiers in this product name are as follows. "K" in the "K100" series grade indicates that the product's grade specifications are on file at the U.S. FDA to support new drug applications. The "100" indicates viscosity and, more specifically, means that a 2% solution of the product in water at 20° C. has viscosity ranging from 78 to 117 MPa·s. "LV" refers to the relative low viscosity properties of the product, and "CR" identifies the product as a "slow release" compound. "LH" refers to "low hygroscopicity/low humidity," a factor which influences properties such as organic solubility and the thermal gelation temperature of aqueous solutions. The "LH" factor prevents excipients from absorbing moisture and aids in prevention of any interaction between the active pharmaceutical ingredient and excess surface moisture from the excipient. The present inventors unexpectedly observed that dosage forms made according to the present disclosure including HPMC K100 LV CR LH as a controlled release agent exhibited significantly improved stability as compared with dosage forms having the same composition and made in the same way but lacking HPMC K100 LV CR LH controlled release agent. The significantly improved stability observed for the immediate release oral dosage form including HPMC K100 LV CR LH was surprising at least because HPMC K100 LV CR LH controlled release agent was not intended for use as an excipient in an immediate release formulation.

The hydrophilic polymer (e.g., HPMC K100 LV CR LH) can be present in the oral dosage form in amounts per 130 mg tablet ranging from about 0.01 mg to about 15 mg, from about 0.1 mg to about 10 mg, from about 1.0 mg to about 5.0 mg, or from about 2.0 mg to about 4.0 mg.

The weight/weight concentration of hydrophilic polymer per oral dosage form (e.g., tablet) according to the present disclosure ranges from about 0.01% to about 15%, from about 0.05% to about 10%, from about 0.1% to about 8%, from about 0.5% to about 10%, from about 0.5% to about 5%, or from about 1% to about 5%, by weight of the oral dosage form.

The antioxidant used in the oral dosage form according to the present disclosure is selected from, but is not limited to, butylated hydroxyanisole (BHA), butylated hydroxytoluene (BHT), ethylenediaminetetraacetic acid (EDTA), sodium metabisulfite, ascorbic acid, citric acid, ascorbyl palmitate, sodium isoascorbate, dihydroguaretic acid, potassium sorbate, sodium bisulfate, sorbic acid, potassium ascorbate, vitamin E, 4-chloro-2,6-diteriarybutylphenol, alphatocopherol, propylgallate, and combinations of two or more thereof.

In certain embodiments, the antioxidant in the oral dosage form includes at least one of butylated hydroxyanisole (BHA), butylated hydroxytoluene (BHT), ethylenediaminetetraacetic acid (EDTA), and sodium metabisulfite.

The antioxidant can be present in 130 mg tablets or other oral dosage forms according to the present disclosure in amounts ranging from about 0.01 mg to about 15 mg, from about 0.1 mg to about 10 mg, from about 1.0 mg to about 5.0 mg, or from about 2.0 mg to about 4.0 mg.

The concentration of antioxidant that can be present per oral dosage form (e.g., tablet) can range from 0.01% to about 5%, from about 0.01% to about 2%, from about 0.05% to about 1.0%, from about 0.1% to about 1.0%, from about 0.15% to about 0.75%, or from about 0.2% to about 0.5%, by weight of the oral dosage form.

An aspect of the present disclosure is directed to methods of administering an oral dosage form according to the present disclosure to a patient in need thereof. According to one method, an immediate oral dosage form according to the present disclosure including a thyroid hormone salt is administered to a patient in need thereof such that that the patient receives about 25 µg, 50 µg, 75 µg, 88 µg, 100 µg, 112 µg, 125 µg, 137 µg, 150 µg, 175 µg, 200 µg, or 300 µg of a levothyroxine salt per dosage.

According to the present disclosure, an immediate release oral dosage form can be prepared by uniformly mixing a thyroid hormone or thyroid hormone salt into a mixture comprising diluents, a hydrophilic polymer, coloring agents, and a glidant, and then subsequently adding an antioxidant to the resulting mixture with additional uniform mixing. The mixture is then screened through a mesh screen and uniformly mixed a second time. A second lubricant is then added to the mixture, the mixture is uniformly mixed a third time, and portions of the mixture are formed into tablets by direct compression. In certain embodiments, a layering process for preparing an oral dosage form can include blending one or more polymers, diluents, and binders, mixing the layered dry mixture with one or more disintegrants, lubricants, and optionally more diluents, discharging the final dry blend using a cradle discharge method, and compressing the dry blend into tablets.

Without intending to be bound by theory, it is believed that the improved stability of oral dosage forms according to the present disclosure is a result of the presence of hydrophilic polymer and antioxidant in a synergistic ratio of weight/weight concentrations.

Figure 1:
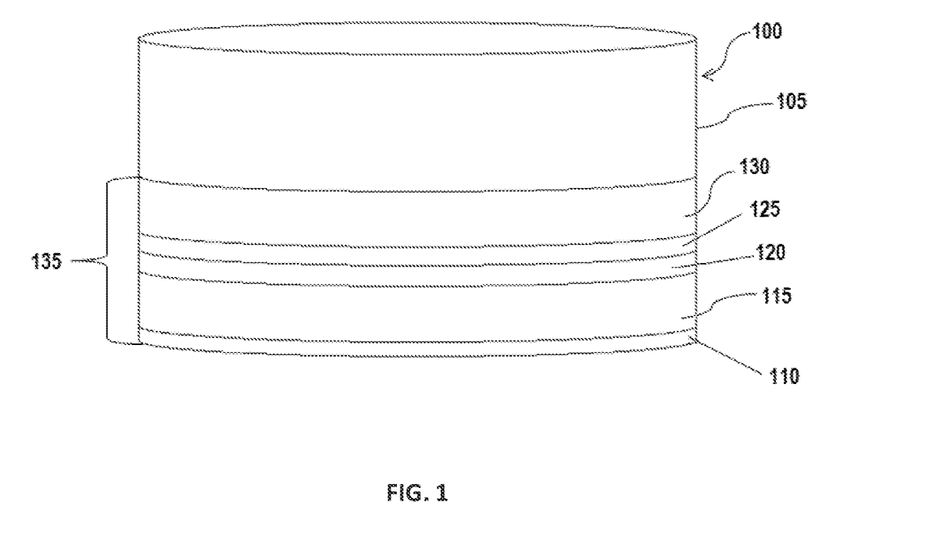
FIG. 1 is a schematic representation of a power granulator containing dry oral dosage form ingredients and used to prepare the oral dosage form by a dry layering/mixing process as described herein.

Embodiments of oral dosage forms according to the present disclosure may be prepared according to the following general process. The general process instructions provided herein are exemplary and should not be considered to be strictly limiting. Oral dosage forms may be prepared using a dry layering/mixing process using a power granulator or a high shear mixer. The power granulator may be of a design having a bottom drive or top drive impeller such as, for example, a Powrex FM-VG-25 Hi-Shear Granulator, manufactured by Powrex Corporation, Hyogo, Japan, or a high shear mixer granulator (HSMG) varying in size from a 0.25 L bowl to a 800 L bowl manufactured by Glat, Collette, Vector, ACG, Fluid air or any vendor making similar granulators. FIG. 1 illustrates a power granulator 105 loaded with dry ingredients 100 which have been arranged in the form of a dry layered blend 135. The dry layered blend is prepared by first screening a diluent (e.g., a biopolymer, such as, for example, AVICEL® HFE-102, available from FMC BioPolymer, Philadelphia, Pa.) through a #30 mesh screen and then mixing the diluent using the power granulator 105 to form a first layer 110 in the power granulator 105. Next, a screened blend is prepared by dry screening an amount of the diluent, one or more colorants (e.g., D&C Yellow No. 10, FD&C Yellow No. 6, and FD&C Blue No. 1), hydrophilic polymer, and glidant (e.g., talc), together to form a screened blend. One half of the total amount of the screened blend is positioned in the power granulator 105 to form a second layer 115 on the first layer 110. A thyroid hormone salt is screened through a #60 mesh screen and disposed as a third layer 120 on the second layer 115 in the power granulator 105. Next, a fourth layer 125 is formed by screening an antioxidant through a #200 mesh screen and depositing it on third layer 120 in the power granulator 105. The remaining one-half of the screened blend is added to the power granulator 105 to form a fifth layer 130 on the fourth layer 125. The dry layered blend 135 comprises the layers 110, 115, 120, 125, and 130. The power granulator 105 is activated to uniformly mix the dry layered blend 135 and thereby form a mixed dry blend. The mixed dry blend is screened through a #30 mesh screen and returned to the power granulator 105 and uniformly mixed once again to form a mixed and screened dry blend. Next, a dry lubricant (e.g., magnesium stearate) is screened through a #30 mesh screen and added to the mixed and screened dry blend, and the combined ingredients are uniformly mixed in the power granulator 105 to form a substantially uniform dry oral dosage mixture. Predetermined quantities of the dry oral dosage mixture are compressed into tablets. Alternatively, predetermined quantities of the dry oral dosage mixture may be disposed in capsules such as, for example, hard gelatin capsules, or used to prepare suitable solid oral dosage forms.

Suitable diluents used in the oral dosage form can include at least one of AVICEL® HFE-102 (microcrystalline cellulose and mannitol); microcrystalline cellulose (MCC); confectioner's sugar (including corn starch); croscarmellose sodium; carbohydrates such as, for example, arabinose, sucrose, dextrose, fructose, maltose, lactose, lactose monohydrate, trehalose, isomalt, starch, monosaccharides, disaccharides, and polysaccharides; and sugar alcohols such as sorbitol, mannitol, erythritol, xylitol, lactitol, and derivatives thereof; and combinations of any thereof.

In a preferred embodiment, a mixture of diluents, AVICEL® HFE-102, is used that can include MCC and mannitol. In certain non-limiting embodiments, the amount of AVICEL® HFE-102 included in a 130 mg tablet or other oral dosage form according to the present disclosure can range from about 75 mg to about 150 mg, from about 82.7 mg to about 137.8 mg, from about 99.19 mg to about 121.19 mg, from about 105.19 mg to about 115 mg, or from about 107 mg to about 112 mg.

In terms of weight/weight concentrations, the level of AVICEL® HFE-102 included in a 130 mg tablet or other oral dosage form according to certain embodiments of the present disclosure can range from about 60% to about 98%, from about 66% to about 92%, from about 70% to about 90%, from about 80% to about 88%, or from about 82% to about 86%, or can be about 82%, about 83%, about 84%, about 84.7%, about 84.76%, about 84.8%, or about 85%, by weight of the oral dosage form.

Examples of suitable glidants that can be used in the oral dosage forms herein include talc, silicon dioxide, colloidal silicon dioxide, stearic acid, magnesium stearate, calcium stearate, hydrogenated castor oil, sucrose esters of fatty acids, microcrystalline wax, yellow beeswax, white beeswax, solid polyethylene glycols, cocoa butter, and combinations of any thereof.

In certain non-limiting embodiments, the amount of glidant used in a 130 mg tablet or other oral dosage form according to the present disclosure can range from about 0.001 mg to about 50 mg, from about 0.01 mg to about 25 mg, from about 0.10 mg to about 15 mg, from about 0.15 mg to about 10 mg, from about 0.25 mg to about 5.0 mg, from about 0.50 mg to about 2.5 mg, or from about 0.75 mg to about 1.5 mg.

In terms of weight/weight concentrations, the level of glidant included in a 130 mg tablet or other oral dosage form according to certain embodiments of the present disclosure can range from about 0.001% to about 50%, from about 0.01% to about 25%, from about 0.10% to about 15%, from about 0.15% to about 10%, from about 0.25% to about 5.0%, from about 0.50% to about 2.0%, or from about 0.70% to about 1.5%, or may be about 0.50%, about 0.6%, about 0.70%, about 0.75%, about 0.77%, about 0.8%, about 0.85%, about 0.9%, about 1.0%, about 2%, about 3%, or about 5%, by weight of the oral dosage form.

Examples of suitable lubricants that can be used in the oral dosage forms herein include sodium stearyl fumarate, polyethylene glycols, sodium stearyl sulfate, cocoa butter, sodium benzoate, talc, colloidal silicon dioxide, stearic acid (and its derivatives or esters such as, for example, sodium stearate, magnesium stearate, calcium stearate), and combinations of any thereof.

In certain non-limiting embodiments, the amount of lubricant included in a 130 mg tablet or other oral dosage form according to the present disclosure can range from about 0.001 mg to about 50 mg, from about 0.01 mg to about 25 mg, from about 0.10 mg to about 15 mg, from about 0.15 mg to about 10 mg, from about 0.25 mg to about 5.0 mg, from about 0.300 mg to about 2.5 mg, or from about 0.40 mg to about 1.0 mg, or can be about 0.20 mg, about 0.300 mg, about 0.40 mg, about 0.45 mg, about 0.50 mg, about 0.55 mg, about 0.60 mg, about 0.70 mg, or about 0.80 mg.

In terms of weight/weight concentrations, the level of lubricant included in a 130 mg tablet or other oral dosage form according to certain embodiments of the present disclosure can range from about 0.001% to about 50%, from about 0.01% to about 25%, from about 0.10% to about 10%, from about 0.2% to about 5.0%, from about 0.3% to about 2.5%, or from about 0.1%, or can be about 0.2%, about 0.3%, about 0.38%, about 0.4%, about 0.5%, about 0.6%, or about 0.7%, by weight of the oral dosage form.

In certain embodiments, the ingredients of the oral dosage form can be uniformly mixed as dry components using a high shear mixer granulator (HSMG), which includes a bottom driven agitator and usually is used for liquid or "wet" granulation. In certain method embodiments, an HSMG is used to dry blend mix the dosage form ingredients using a specific purge setting in the range of, for example, 0.01 to 1.0 bars, 0.03 to 0.07 bars, or 0.05 to 0.5 bars. In certain preferred embodiments, the purge setting is in the range of 0.05 to 0.5 bars or 0.3 to 0.5 bars. Discharge of the mixture from the HSMG may be completed using, for example, a cradle discharge method in which small quantities of the uniform mixture are discharged from the HSMG over a short period of time (e.g., 2 to 10 seconds or 20 to 30 seconds) to prevent segregation.

A tablet or other oral dosage form according to the present disclosure including a thyroid hormone salt has been observed to exhibit unexpectedly improved stability. In particular, it has been observed that such oral dosage forms retain at least 100% of the initial amount of thyroid hormone salt after storage for at least six months at standard testing conditions of 23° C. to about 27° C. and a relative humidity ranging from about 55% to about 65%. Under intermediate testing conditions, it was observed that the oral dosage forms retained at least 100% of the initial amount of thyroid hormone salt after storage for at least six months at a temperature ranging from about 28° C. to 32° C. and a relative humidity of about 60% to about 70%. Under accelerated stability testing conditions, it was observed that the oral dosage forms retained at least 95% of the initial amount of thyroid hormone salt after storage for at least six months at a temperature ranging from about 38° C. to about 42° C. and a relative humidity ranging from about 70% to about 80%. It was also observed that at temperatures ranging from about 58° C. to about 62° C., the oral dosage forms retained at least 95% of the initial amount of thyroid hormone salt for at least fifteen days when purged with nitrogen during packaging to prevent interaction of the thyroid hormone salt with environmental oxygen during the packaging process.

In certain embodiments, oral dosage forms according to the present disclosure retain at least 95% of the initial amount of thyroid hormone salt after storage for one month, four months, six months, eight months, one year, eighteen months, or two years under normal stability testing conditions including a temperature ranging from about 23° C. to about 27° C. and a relative humidity ranging from about 55% to about 65%. In certain embodiments, oral dosage forms according to the present disclosure as disclosed herein retain at least 95% of the initial amount of thyroid hormone salt after storage for four months, six months, eight months, one year, eighteen months, or two years under accelerated stability testing conditions including a temperature ranging from about 38° C. to about 42° C. and a relative humidity ranging from about 70% to about 80%.

NON-LIMITING EXAMPLES

Example 1

Figure 2:
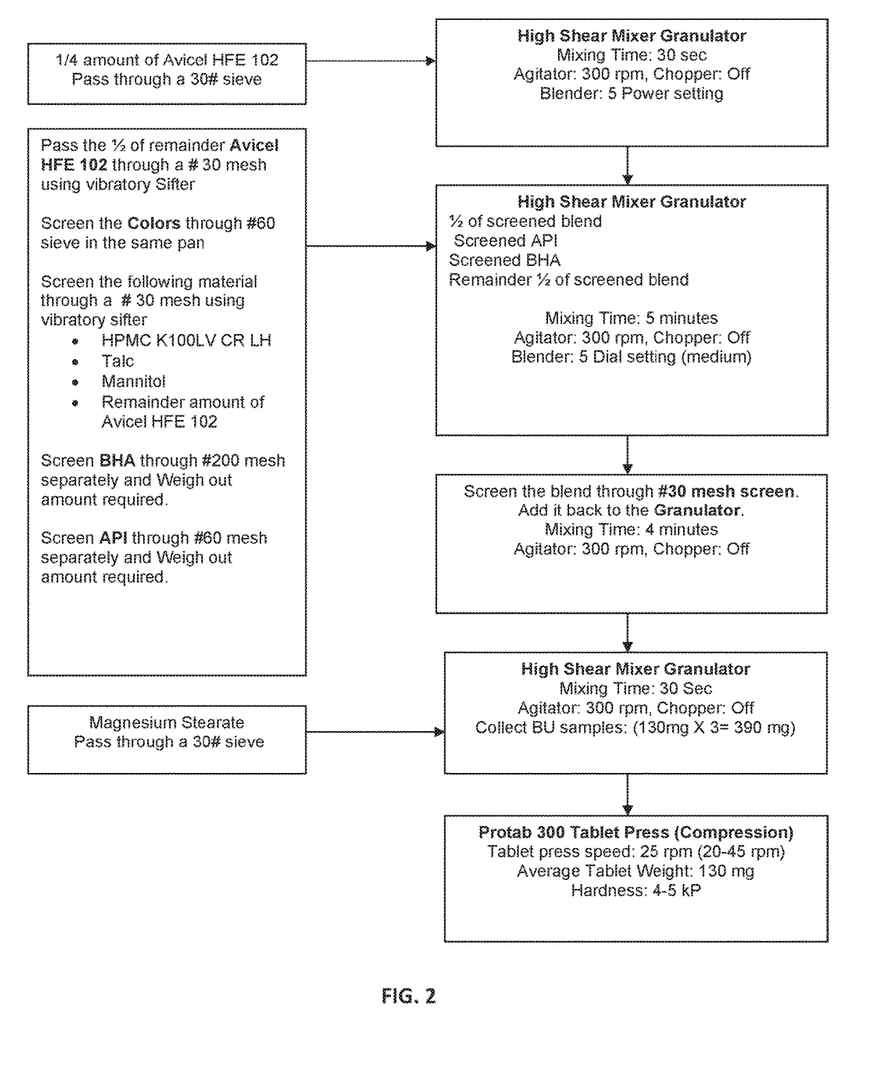
FIG. 2 is a schematic representation of the manufacturing process of the pharmaceutical composition described herein.

FIG. 2 generally illustrates the dry layering/mixing and tableting process for preparing a levothyroxine sodium oral tablet, and this process is discussed in detail below.

Twenty five percent of a total required amount of AVICEL® HFE-102 material was screened through a #30 mesh screen, and the screened material was then mixed in a high shear mixer granulator (HSMG) (Powrex FM-VG-25 Hi-Shear Granulator) for thirty seconds at a power setting of 5 (500 rpms per minute) with amperage at 3-4 amperes. The screened and mixed portion of the AVICEL® HFE-102 material formed a first layer in the HSMG.

Next, a screened blend was prepared by dry screening through a #30 mesh screen into a vessel the remaining 75% of the total needed amount of AVICEL® HFE 102 material, the three colorants (D&C Yellow #10, FD&C Yellow #6, and FD&C Blue No. 1, all previously screened through a #60 mesh screen), the HPMC K-100 LV CR LH, mannitol, and talc. One half of the total amount of this screened blend was positioned in the HSMG to form a second layer adjacent to the first (AVICEL® HFE-102 material) layer.

Next, the levothyroxine sodium was screened through a #60 mesh screen and disposed on the second layer in the HSMG to form a third layer adjacent to the second (screened blend) layer.

Next, the BHA was screened through a #200 mesh screen and added to the HSMG as a fourth layer adjacent to the third (levothyroxine sodium) layer.

Next, the remaining half of the screened blend was added to the HSMG to form a fifth layer adjacent to the fourth (BHA) layer.

The assembly of five layers disposed in the HSMG constituted a dry layered blend. The HSMG was activated to uniformly mix the dry layered blend for five minutes using a HSMG dial setting of 5 (500 rpms per minute) with amperage at 3-4 amperes. The HSMG was operated under low purge air pressure of 0.02 psi. The mixed dry layered blend was removed from the HSMG and screened through a #30 mesh screen and returned to the HSMG for further uniform mixing for four minutes using an HSMG setting of 5 (500 rpm per minute) with amperage at 3-4 amperes Magnesium stearate was screened through a #30 mesh screen and added to the doubly mixed and screened dry layered blend, and the materials were uniformly mixed for 30 seconds using an HSMG setting of 5 (500 rpms per minute) with amperage at 3-4 amperes to form a final oral dosage mixture.

Portions of the final oral dosage mixture were removed from the HSMG using a cradle discharge method. The cradle discharge method removed multiple small quantities of the final oral dosage mixture from the HSMG over short time periods to prevent segregation of the ingredients. Finally, measured portions of the dry oral dosage mixture were compressed into 130 mg tablets using a Piccola/Globe pharma tablet press. These were compressed to a hardness of 4-5 Kp.

The tablets were then packaged in either 75 $cm^3$ or 300 $cm^3$ high density polyethylene bottles. For 75 $cm^3$ bottles, 90 to 100 tablets were packaged with three, 2 g SORB-IT® silica gel desiccant canisters (commercially available from CLARIANT INTERNATIONAL LTD, Colton, Calif.) (6 g total). For 300 $cm^3$ bottles, about 1000 tablets were packaged with eight, 2 g SORB-IT® silica gel desiccant canisters (16 g total).

Example 2

A study was conducted to assess the stability of oral dosage forms prepared by the method disclosed in Example 1.

Oral dosage forms were prepared by compressing portions of uniform mixtures made using the dry layering/mixing method generally described in Example 1 above into individual 130 mg tablets. Each of the mixtures included levothyroxine sodium, the hydrophilic polymer HPMC K100 LV CR LH, and the antioxidant butylated hydroxy anisole (BHA).

Table 1 below provides the composition of 130 mg tablets produced in Batches 164 and 168.

TABLE 1

Composition of 130 mg levothyroxine sodium tablets prepared in Batches 164 and 168 (identical compositions).

| Ingredients | % w/w | mg/unit |
| --- | --- | --- |
| Levothyroxine Sodium | 0.23 | 0.30 |
| Avicel HFE 102 | 84.76 | 110.19 |
| Mannitol | 11.27 | 14.65 |
| HPMC K100 LV CR LH | 2.318 | 3.00 |
| Butylated Hydroxy Anisole (BHA) | 0.23 | 0.30 |
| D&C Yellow No. 10 Aluminium Lake | 0.017 | 0.022 |
| FD&C Yellow No. 6 Aluminium Lake | 0.004 | 0.005 |

TABLE 1-continued

Composition of 130 mg levothyroxine sodium tablets prepared in Batches 164 and 168 (identical compositions).

| Ingredients | % w/w | mg/unit |
|---|---|---|
| FD&C Blue No. 1 Aluminium Lake | 0.025 | 0.033 |
| Talc | 0.77 | 1.00 |
| Magnesium Stearate | 0.38 | 0.50 |
| Total | 100.00 | 130.00 |

Figure 5:
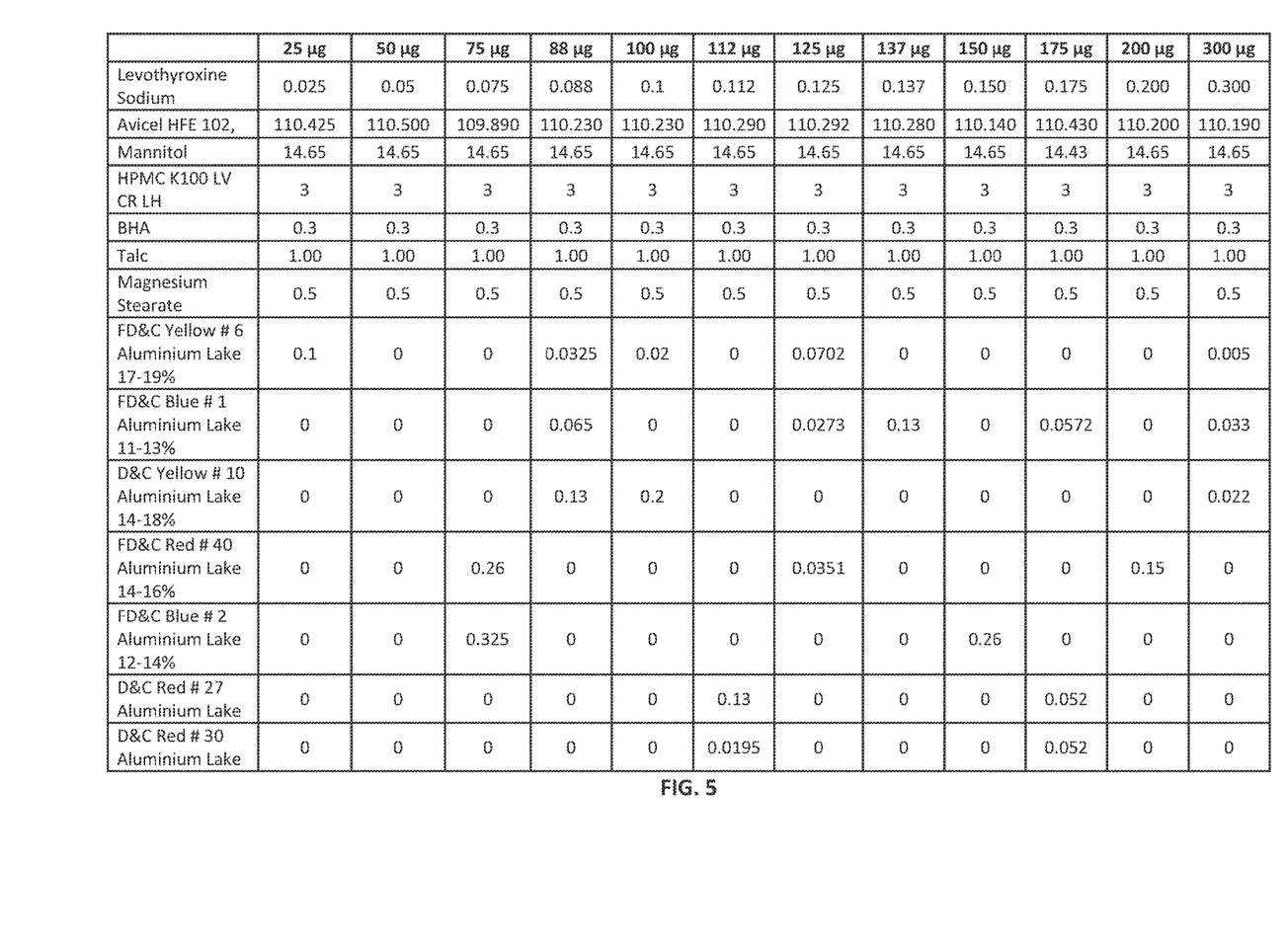
FIG. 5 represents exemplary formulations for levothyroxine sodium tablets.

Compositions with different amounts of the active agent may be formed in a dose similar manner by adjusting the amount of the active ingredient, along with the amount of an inactive ingredient, along with coloring agents to keep the mass of the dosage forms the same. Exemplary formulations for oral tablets with 25 μg, 50 μg, 75 μg, 88 μg, 100 μg, 112 μg, 125 μg, 137 μg, 150 μg, 175 μg, 200 μg, or 300 μg of levothyroxine sodium are shown in FIG. 5. Different tablet strengths may utilize different colorants to produce tablets of different colors.

For purposes of conducting a stability study, the oral dosage form tablets in Batch 168 were disposed in the 75 cm$^3$ (100 count) and 300 cm$^3$ (1000 count) container closure system containing 2 gm SORB-IT® desiccant silica gel canisters and a closure. The container closure system included either three or eight 2 gm SORB-IT® desiccant silica gel canisters (total of 6 gm or 16 gm desiccant, respectively) and the closure. Either 100 or 1000 tablets were disposed in each container. Once filled with tablets, each container closure system was induction sealed with nitrogen purging to prevent interaction of the levothyroxine sodium in the oral dosage form tablets with environmental oxygen during the packaging process. Optionally, air space may be displaced with an inert pill packing material, for example, rayon or cotton.

Three studies were conducted to assess the stability of the levothyroxine sodium in the oral dosage form tablets of Batch 168. The stability studies involved the following testing periods and conditions:

Standard testing conditions (25° C.±2° C. and 60%±5% relative humidity) for up to six months.

Accelerated testing conditions (40° C.±2° C. and 75%±5% relative humidity) for up to three months.

Extreme testing conditions (60° C.±2° C.) for 15 days.

A standard testing conditions stability study of the oral dosage form tablets of Batch 168 contained in the container closure system was conducted over a period of six months to determine the rate of physical or chemical degradation of the 0.300 mg of levothyroxine sodium included in the oral dosage form tablets of Batch 168 over standard environmental conditions.

All standard testing conditions stability samples (each sample consisting of a container closure system containing either 100 or 1000 count bottles of oral dosage form tablets of Batch 168, including 0.300 mg of levothyroxine sodium per dosage form) were placed upright in an environmental chamber and maintained in an upright position during the stability study. All of the containers were maintained at 25° C.±2° C. and 60%±5% relative humidity conditions, uninterrupted, (except for the addition or withdrawal of test samples) for a period of one, two, three or six months. Samples were removed from conditions at the specified time point and tested for levothyroxine sodium content. Storage of the stability samples was completed using a calibrated environmental chamber. Testing of the stability samples was completed using High Pressure Liquid Chromatography.

Shelf life of the levothyroxine sodium contained in the 100 count bottle of oral dosage form tablets was estimated to be at least six months at ambient conditions, based upon the six month term stability assay results shown in Table 2 for the oral dosage form tablets of Batch 168. The stability assay showed that greater than 99 percent of the original levothyroxine sodium was retained in the oral dosage form tablets in the 100 count bottle over the course of the standard testing conditions for six months.

Shelf life of the levothyroxine sodium oral dosage form tablets of Batch 168 contained in the 1000 count bottle was estimated to be at least one month at ambient conditions, based on the one month term stability assay results shown in Table 4. The stability assay showed 101.0 percent of the original levothyroxine sodium was retained in the oral dosage form tablets in the 1000 count bottle over the course of the standard stability conditions assay for one month.

Tables 2 and 3 report stability data for the oral dosage form samples (Batch 168) tested under standard, accelerated, and extreme conditions. In Tables 2 and 3, To refers to time zero.

TABLE 2

Stability data results for the oral dosage form tablets of Batch 168 including 0.300 mg of levothyroxine sodium in 75 cm$^3$, 100 count bottles at standard testing conditions, accelerated testing conditions, and extreme testing conditions over a period of 15 days, 1, 2, 3, and 6 months.

| Time Period | Testing Conditions | Desiccant (gm) | Assay % | Nitrogen Purge |
|---|---|---|---|---|
| T$_0$ | N/A | 6 | 100.5 | Yes |
| 15 Days | 60° C./0% RH | 6 | 96.1 | Yes |
| 1 Month | 25° C./60% RH | 6 | 100.9 | Yes |
| 1 Month | 40° C./75% RH | 6 | 99.6 | Yes |
| 2 Months | 25° C./60% RH | 6 | 100.4 | Yes |
| 2 Months | 40° C./75% RH | 6 | 98.7 | Yes |
| 3 Months | 25° C./60% RH | 6 | 99.8 | Yes |
| 3 Months | 40° C./75% RH | 6 | 95.9 | Yes |
| 6 Months | 25° C./60% RH | 6 | 99.5 | Yes |

TABLE 3

Stability data results for the oral dosage form tablets of Batch 168 including 0.300 mg of levothyroxine sodium in 300 cm$^3$, 1000 count bottles at standard testing conditions and accelerated testing conditions, over a period of 1 month.

| Time Period | Testing Conditions | Desiccant (gm) | Assay % | Nitrogen Purge |
|---|---|---|---|---|
| T$_0$ | N/A | 16 | 100.5 | |
| 1 Month | 25° C./60% RH | 16 | 101.0 | Yes |
| 1 Month | 40° C./75% RH | 16 | 100.2 | Yes |

As indicated in Tables 2 and 3, an accelerated stability study of the same manufactured Batch 168 oral dosage form tablets as used in the standard testing conditions stability study was conducted over certain periods (one, two, or three months) to determine the rate of physical or chemical degradation of the oral dosage form tablets including 0.300 mg of levothyroxine sodium over accelerated environmental conditions.

All accelerated stability samples (each sample comprising a container closure system including either 100 or 1000 oral dosage form tablets of Batch 168, each tablet originally including 0.300 mg of levothyroxine sodium) were placed upright in an environmental chamber and maintained in an upright position during the stability study. All of the containers were maintained at 40° C.±2° C. and 75%±5% relative humidity conditions, uninterrupted, (except for the addition or withdrawal of test samples) for a period of one, two, or three months. Samples were removed from conditions at the specified time point and tested for levothyroxine sodium content. Storage of the stability samples was completed using a calibrated environmental chamber. Testing of the stability samples was completed using High Pressure Liquid Chromatography.

Shelf life of the levothyroxine sodium oral dosage form tablets of Batch 168 contained in the 100 count bottle of oral dosage form tablets was estimated to be at least three months at the accelerated testing conditions, based on the three months term stability assay results shown in Table 2 for the oral dosage form tablets of Batch 168. The stability assay of the tablets of Batch 168 in the 100 count bottle showed that 95.9 percent of the levothyroxine sodium was retained in the oral dosage form tablets over the course of the accelerated testing conditions stability assay for three months.

Shelf life of the levothyroxine sodium oral dosage form tablets of Batch 168 contained in the larger scale 1000 count bottle was estimated to be at least one month at the accelerated testing conditions, based on the one month term stability assay results shown in Table 3. The stability assay of the oral dosage for tablets of Batch 168 in the 1000 count bottle showed that 100.2 percent of the levothyroxine sodium was retained in the oral dosage form tablets over the course of the accelerated testing conditions stability assay for one month.

An extreme stability study of the same manufactured Batch 168 oral dosage form tablets as evaluated in the standard testing conditions stability study was conducted over a period of 15 days to determine the rate of physical or chemical degradation of the oral dosage form tablets initially including 0.300 mg of levothyroxine sodium over extreme environmental conditions.

All extreme stability samples (each sample containing oral dosage form tablets of Batch 168, initially including 0.300 mg of levothyroxine sodium) were placed upright in an environmental chamber and maintained in an upright position during the stability study. All of the containers were maintained at 60° C.±2° C., uninterrupted (except for the addition or withdrawal of test samples), for a period of 15 days. Samples were removed from conditions at the specified time point and tested for levothyroxine sodium content. Storage of the stability samples was completed using a calibrated environmental chamber. Testing of the stability samples was completed using High Pressure Liquid Chromatography.

Shelf life of the levothyroxine sodium oral dosage form tablets of Batch 168 in the 100 count container was estimated to be at least 15 days at the extreme testing conditions, based upon the stability assay results shown in Table 2. The stability assay showed that greater than 96 percent of the levothyroxine sodium was retained in the oral dosage form tablets over the course of the extreme testing conditions stability assay for 15 days.

Based on the results shown in Table 2, the inventor surprisingly discovered that the oral dosage form tablets of Batch 168 in the 100 count bottle retained 99.5% of the levothyroxine sodium under standard testing conditions at 25° C.±2° C. and 60%±5% relative humidity for a period of six months. Even under accelerated conditions (40° C.±2° C. and 75%±5% relative humidity) over the course of three months, the results showed retention of more than 95.9% of the levothyroxine sodium (a decrease in the levothyroxine sodium content of the tablets of less than five percent).

Example 3

The effects on levothyroxine sodium stability by investigating the impact of nitrogen purging were studied. In the stability study of this example, tablet-filled containers were induction sealed either with or without nitrogen purging.

Methods and Materials

The 130 mg oral dosage form tablets of Batch 164 were disposed in the container closure system, providing a packaged oral dosage form, for purposes of conducting the stability study to determine the effect of nitrogen purging as a part of the packaging configuration.

Figure 3:
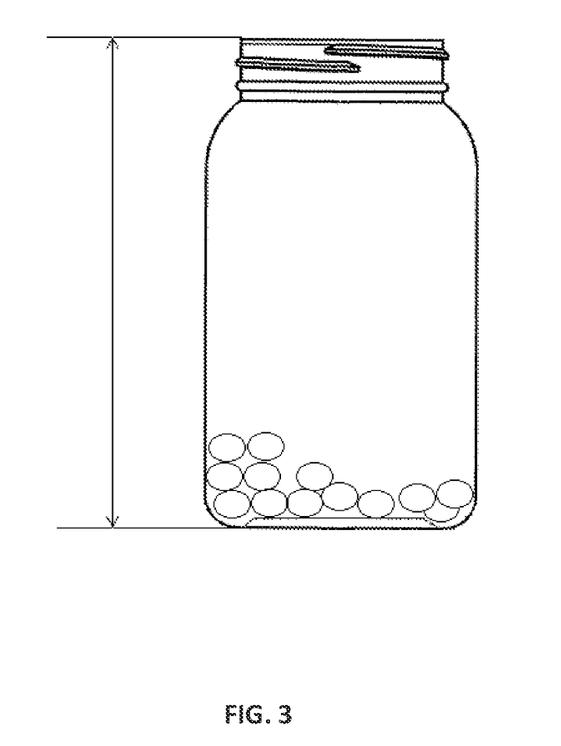
FIG. 3 is a side view of a high density polyethylene container used to contain a pharmaceutical composition, as described herein.
Figure 4A:
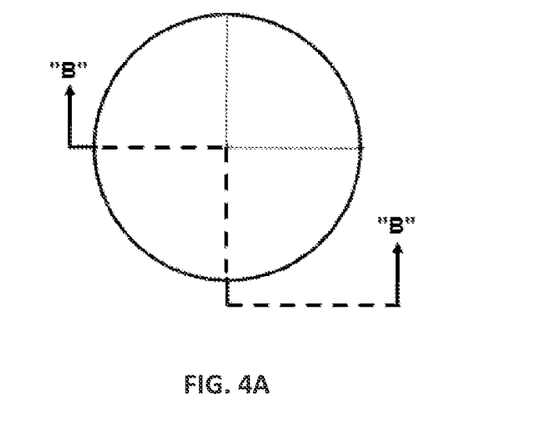
Figure 4B:
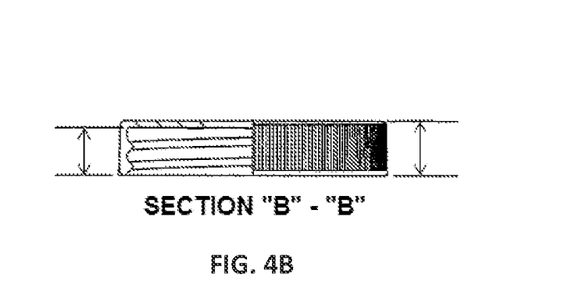

The container closure system (including a 75 $cm^3$ bottle) contained 100 tablets from Batch 164 along with three 2 gm SORB-IT® desiccant silica gel canisters (total of 6 gm desiccant) and included a closure for sealing the container. FIGS. 3A, 3B, 4A, and 4B depict the container and closure system.

The stability study was conducted over a one week and one month period to determine the rate of physical or chemical degradation of levothyroxine sodium in the oral dosage form tablets. The sealed containers were placed upright in an environmental chamber and maintained in an upright position during the study. One set of the containers were maintained at 60° C.±2° C., for one week, uninterrupted until sampled. Another set of the containers were maintained for one month at either 25° C.±2° C. and a 60%±5% relative humidity or 40° C.±2° C. and a 75%±5% relative humidity. At the time of sampling, the tablets were removed from each container and tested for levothyroxine sodium content using high pressure liquid chromatography.

Results

Table 4 reports the stability test results for the Batch 164 oral dosage form tablets stored in the container closure system with and without nitrogen purging during the packaging process. In the Table, $T_0$ refers to time zero.

TABLE 4

Stability results for Batch 164 stored in the modified container closure system.

| Time Period | Testing Conditions | Desiccant (gm) | Assay % | Nitrogen Purge |
|---|---|---|---|---|
| $T_0$ | N/A | — | 98.2 | Yes |
| 7 Days | 60° C | 6 | 94.2 | Yes |
| 7 Days | 60° C | 6 | 93.3 | No |
| 1 Month | 25° C./60% RH | 6 | 98 | Yes |
| 1 Month | 25° C./60% RH | 6 | 97.9 | No |
| 1 Month | 40° C./75% RH | 6 | 97.4 | Yes |
| 1 Month | 40° C./75% RH | 6 | 96.4 | No |

The results from Table 4 demonstrate that the closure systems sealed under nitrogen purging during the packaging process exhibited increased stability of the levothyroxine sodium content under all conditions tested within the oral dosage form tablets of Batch 164. This result demonstrates the effectiveness of replacement of environmental oxygen with inert nitrogen within the container closure system.

Example 4

A study was conducted to compare different types of desiccants, PHARMAKEEP® or SORB-IT®.

SORB-IT® is a packaged silica gel desiccant that is made from amorphous silicate. It is a hard, translucent material with a high capacity for moisture at temperatures below 75° C. and humidity levels about 40% RH. SORB-IT® is designed to control moisture levels within packaged products, such as pharmaceuticals.

PHARMAKEEP® is available as canisters and packets. PHARMAKEEP® is an oxygen absorbing desiccant that protects pharmaceutical and diagnostic products from oxygen degradation and oxidative reactions. PHARMAKEEP® does not require humidity to function and can also be used in conjunction with other desiccants.

The 130 mg tablets in Batches NB 527-111 and NB 527-117 were prepared using the method described above, and these tablets are identical to the composition described in Table 1. These tablets were stored at 40° C. at 75% RH for a period of one month. Each batch was stored separately with either PHARMAKEEP® desiccants or SORB-IT® desiccants.

Table 5 reports the stability test results for oral dosage form tablets of Batch NB 527-111 stored with PHARMAKEEP® or SORB-IT® desiccants and for oral dosage form tablets of Batch NB 527-117 stored with PHARMAKEEP® or SORB-IT® desiccants.

TABLE 5

Stability Results with Different Desiccants (PHARMAKEEP ® v. SORB-IT ®)

| Batch No. | Time Point | Stability Condition | Desiccant type | % Assay |
|---|---|---|---|---|
| NB 527:111 | 1 Month | 40° C./75% RH | PHARMAKEEP ® | 95.0 |
| | 1 Month | 40° C./75% RH | SORB-IT ® | 97.6 |
| NB 527:117 | 1 Month | 40° C./75% RH | PHARMAKEEP ® | 94.8 |
| | 1 Month | 40° C./75% RH | SORB-IT ® | 97.4 |

The results from Table 5 demonstrate that the use of SORB-IT® exhibited increased stability of the levothyroxine sodium content within the oral dosage form tablets of Batch NB 527-117 compared to PHARMAKEEP®. This result demonstrates the effectiveness of replacement of environmental oxygen with inert nitrogen within the container closure system.

Example 5

A study was conducted to determine the optimum amount of desiccant to include in a 100 count bottle.

The 130 mg tablets in Batch 164 were prepared using the method described above, and these tablets are disclosed as the composition described in Table 1. These tablets were stored at extreme conditions at 60° C. Each batch was stored separately with either 4 g or 6 g of SORB-IT® desiccant silica gel canisters.

Table 6 reports the stability test results for oral dosage form tablets of Batch 164 stored with either 4 g or 6 g of desiccant. $T_0$ refers to time zero.

TABLE 6

Stability Results with Different Amount of Desiccant

| Time Point | Stability Condition | Amount of Desiccant (g) | % Assay |
|---|---|---|---|
| $T_0$ | N/A | N/A | 98.2 |
| 7 days | 60° C. | 4 g | 93.3 |
| 7 days | 60° C. | 4 g | 92.8 |
| 7 days | 60° C. | 6 g | 94.2 |
| 7 days | 60° C. | 6 g | 93.3 |

The results from Table 6 demonstrate that the use of 6 g of desiccant exhibited increased stability of the levothyroxine sodium content within the oral dosage form tables of Batch 164 compared to 4 g of desiccant. This result demonstrates the effectiveness of 6 g of desiccant within the container closure system. Similar results are achieved with 16 g of desiccant used within a 300 cm$^3$ container closure system containing 1000 tablets.

Example 6

Studies were conducted to assess the stability of three different batches of oral dosage form tablets prepared by the method of Example 1 and packaged based on the studies performed in Examples 3, 4, and 5. 130 mg oral dosage forms of Batch NB 527-176, representing at ten-fold increase in batch size compared to batch 164, Pilot Batch C51100117 and Pilot Batch C51100217 were prepared using the principles described in Example 1 and have the same composition disclosed in Table 1.

Methods and Materials

For purposes of conducting a stability study, the oral dosage form levothyroxine sodium tablets were disposed in 75 cm$^3$ (100 count) and 300 cm$^3$ (1000 count) container closure systems containing multiple 2 gm SORB-IT® desiccant silica gel canisters and a closure. The container closure system included either three or eight 2 gm SORB-IT® desiccant silica gel canisters (total of 6 gm or 16 gm desiccant, respectively) and the closure. Either 100 or 1000 tablets from a single batch were disposed in each container. Once filled with tablets, each container closure system was induction sealed with nitrogen purging to prevent interaction of the levothyroxine sodium in the oral dosage form tablets with environmental oxygen during the packaging process.

Three studies were conducted on each batch to assess the stability of the levothyroxine sodium in the oral dosage form tablets. The stability studies involved the following testing periods and conditions:

Standard testing conditions (25° C.±2° C. and 60%±5% relative humidity) for up to six months.

Intermediate testing conditions (30° C.±2° C. and 65%±5% relative humidity) for up to six months.

Accelerated testing conditions (40° C.±2° C. and 75%±5% relative humidity) for up to six months.

A standard testing conditions stability study of the oral dosage form tablets contained in the container closure system was conducted over a period of three months to determine the rate of physical or chemical degradation of the 0.300 mg of levothyroxine sodium included in the oral dosage form tablets over standard environmental conditions.

All standard testing conditions stability samples (each sample consisting of a container closure system containing either 100 or 1000 count bottles of oral dosage form tablets, including 0.300 mg of levothyroxine sodium per dosage form) were placed upright in an environmental chamber and maintained in an upright position during the stability study.

All of the containers were maintained at 25° C.±2° C. and 60%±5% relative humidity conditions, 30° C.±2° C. and 65%±5% relative humidity conditions, or 40° C.±2° C. and 75%±5% relative humidity conditions, uninterrupted, (except for the addition or withdrawal of test samples) for a period of one, two, three, or six months. Samples were removed from conditions at the specified time point and tested for levothyroxine sodium content. Storage of the stability samples was completed using a calibrated environmental chamber. Testing of the stability samples was completed using High Pressure Liquid Chromatography.

Results

Tables 7 and 8 report stability data for the oral dosage form samples tested under standard and accelerated conditions.

Table 7 reports the stability test results for Batch NB 527-176 100 oral dosage form tablets stored in the 75 cm$^3$ container closure system (100 count bottle) with nitrogen purging during the packaging process. In Table 7, $T_0$ refers to time zero.

TABLE 7

Stability data results for the 130 mg oral dosage form tablets in 75 cm$^3$, 100 count bottles at standard testing conditions, intermediate testing conditions, and accelerated testing conditions over a period of 1, 2, 3, or 6 months.

| Time Period | Testing Conditions | Desiccant (gm) | Assay % | Nitrogen Purge |
|---|---|---|---|---|
| $T_0$ | N/A | Composite sample | 101.3 | Yes |
| 1 Month | 25° C./60% RH | 6 | 100.2 | Yes |
| 1 Month | 30° C./65% RH | 6 | 100.3 | Yes |
| 1 Month | 40° C./75% RH | 6 | 99.7 | Yes |
| 2 Months | 25° C./60% RH | 6 | 100.3 | Yes |
| 2 Months | 40° C./75% RH | 6 | 98.8 | Yes |
| 3 Months | 25° C./60% RH | 6 | 99.6 | Yes |
| 3 Months | 30° C./65% RH | 6 | 99.9 | Yes |
| 3 Months | 40° C./75% RH | 6 | 96.9 | Yes |
| 6 Months | 25° C./60% RH | 6 | 99.9 | Yes |
| 6 Months | 30° C./65% RH | 6 | 99.4 | Yes |
| 6 Months | 40° C./75% RH | 6 | 94.2 | Yes |

Table 8 reports the stability test results for oral dosage form tablets of Batch NB 527-176 stored in the 300 cm$^3$ container closure system (1000 count bottle) with nitrogen purging during the packaging process. In the table, $T_0$ refers to time zero.

TABLE 8

Stability data results for the 130 mg oral dosage form tablets in 300 cm$^3$, 1000 count bottles at standard testing conditions, intermediate testing conditions, and accelerated testing conditions, over a period of 1, 2, 3, or 6 months.

| Time Period | Testing Conditions | Desiccant (gm) | Assay % | Nitrogen Purge |
|---|---|---|---|---|
| $T_0$ | N/A | 16 | 101.3 | Yes |
| 1 Month | 25° C./60% RH | 16 | 99.2 | Yes |
| 1 Month | 30° C./65% RH | 16 | 99.9 | Yes |
| 1 Month | 40° C./75% RH | 16 | 98.4 | Yes |
| 2 Months | 25° C./60% RH | 16 | 100.9 | Yes |
| 2 Months | 40° C./75% RH | 16 | 98.6 | Yes |
| 3 Months | 25° C./60% RH | 16 | 99.8 | Yes |
| 3 Months | 30° C./65% RH | 6 | 99.5 | Yes |
| 3 Months | 40° C./75% RH | 6 | 97.1 | Yes |
| 6 Months | 25° C./60% RH | 6 | 99.9 | Yes |
| 6 Months | 40° C./75% RH | 6 | 94.7 | Yes |

Shelf life of the levothyroxine sodium contained in the 100 count bottle of oral dosage form tablets was estimated to be at least six months at ambient conditions, based upon the six month term stability assay results shown in Table 7 for the oral dosage form tablets. The stability assay showed that greater than 99 percent of the original levothyroxine sodium was retained in the oral dosage form tablets in the 100 count bottle over the course of the standard stability conditions assay for six months.

Shelf life of the levothyroxine sodium oral dosage form tablets contained in the 1000 count bottle was estimated to be at least six months at ambient conditions based upon the six month term stability assay results shown in Table 8 for the oral dosage form tablets. The stability assay showed that more than 99 percent of the original levothyroxine sodium was retained in the oral dosage form tablets in the 1000 count bottle over the course of the standard stability conditions assay for six months.

As indicated in Table 7, an intermediate stability study of the same manufactured oral dosage form tablets as used in the standard testing conditions stability study was conducted over certain periods (one, two, three, or six months) to determine the rate of physical or chemical degradation of the oral dosage form tablets including 0.300 mg of levothyroxine sodium over accelerated environmental conditions.

Shelf life of the levothyroxine sodium oral dosage form tablets contained in the 100 count bottle of oral dosage form tablets was estimated to be at least six months at the accelerated testing conditions, based on the six month term stability assay results shown in Table 7 for the oral dosage form tablets. The stability assay of the tablets in the 100 count bottle showed that 99 percent of the levothyroxine sodium was retained in the oral dosage form tablets over the course of the accelerated testing conditions stability assay for three months.

As indicated in Tables 7 and 8, an accelerated stability study of the same manufactured oral dosage form tablets as used in the standard testing conditions stability study was conducted over certain periods (one, two, three, or six months) to determine the rate of physical or chemical degradation of the oral dosage form tablets including 0.300 mg of levothyroxine sodium over accelerated environmental conditions.

The stability assay of the tablets in the 100 count bottle showed that 94.2 percent of the levothyroxine sodium was retained in the oral dosage form tablets over the course of the accelerated testing conditions stability assay for six months.

The stability assay of the oral dosage for tablets in the 1000 count bottle showed that 94.7 percent of the levothyroxine sodium was retained in the oral dosage form tablets over the course of the accelerated testing conditions stability assay for six months.

Based on the results shown in Table 7, the inventors surprisingly discovered that the oral dosage form tablets in the 100 count bottle retained 99.9% of the levothyroxine sodium under standard testing conditions at 25° C.±2° C. and 60%±5% relative humidity for a period of six months. Even under accelerated conditions (40° C.±2° C. and 75%±5% relative humidity) over the course of six months, the results showed retention of more than 94% of the levothyroxine sodium.

Table 8 illustrates similar results, where the oral dosage form tablets in the 1000 count bottle retained 99.9% of the levothyroxine sodium under standard testing conditions at 25° C.±2° C. and 60%±5% relative humidity for a period of six months. Even under accelerated conditions (40° C.±2° C. and 75%±5% relative humidity) over the course of six months, the results showed retention of more than 94% of the levothyroxine sodium.

Table 9 reports the stability test results for Pilot Batch NB C51100117 100 oral dosage form tablets stored in the 75 cm³ container closure system (100 count bottle) with nitrogen purging during the packaging process. In Table 9, $T_0$ refers to time zero.

TABLE 9

Stability data results for the 130 mg oral dosage form tablets in 75 cm³, 100 count bottles at standard testing conditions, intermediate testing conditions, and accelerated testing conditions over a period of 1, 2, 3, 4, 5 and 6 months.

| Time Period | Testing Conditions | Desiccant (gm) | Assay % | Nitrogen Purge |
|---|---|---|---|---|
| $T_0$ | N/A | 6 | 102.4 | Yes |
| 1 Month | 25° C./60% RH | 6 | 101.3 | Yes |
| 1 Month | 30° C./65% RH | 6 | 101.3 | Yes |
| 1 Month | 40° C./75% RH | 6 | 100.8 | Yes |
| 2 Months | 25° C./60% RH | 6 | 102.0 | Yes |
| 2 Months | 30° C./65% RH | 6 | 101.6 | Yes |
| 2 Months | 40° C./75% RH | 6 | 99.9 | Yes |
| 3 Months | 25° C./60% RH | 6 | 102.1 | Yes |
| 3 Months | 30° C./65% RH | 6 | 100.8 | Yes |
| 3 Months | 40° C./75% RH | 6 | 98.7 | Yes |
| 4 Months | 25° C./60% RH | 6 | 100.8 | Yes |
| 4 Months | 30° C./65% RH | 6 | 100.4 | Yes |
| 4 Months | 40° C./75% RH | 6 | 97.7 | Yes |
| 5 Months | 25° C./60% RH | 6 | 101.1 | Yes |
| 5 Months | 30° C./65% RH | 6 | 101.2 | Yes |
| 5 Months | 40° C./75% RH | 6 | 96.5 | Yes |
| 6 Months | 25° C./60% RH | 6 | 101.6 | Yes |
| 6 Months | 30° C./65% RH | 6 | 101.0 | Yes |
| 6 Months | 40° C./75% RH | 6 | 95.0 | Yes |

Table 10 reports the stability test results for Pilot Batch C51100217 100 oral dosage form tablets stored in the 75 cm³ container closure system (100 count bottle) with nitrogen purging during the packaging process. In Table 10, $T_0$ refers to time zero.

TABLE 10

Stability data results for the 130 mg oral dosage form tablets in 75 cm³, 100 count bottles at standard testing conditions, accelerated testing conditions, and extreme testing conditions over a period of 1, 2, 3, 4, and 5 months.

| Time Period | Testing Conditions | Desiccant (gm) | Assay % | Nitrogen Purge |
|---|---|---|---|---|
| $T_0$ | N/A | 6 | 101.6 | Yes |
| 1 Month | 25° C./60% RH | 6 | 101.3 | Yes |
| 1 Month | 30° C./65% RH | 6 | 101.2 | Yes |
| 1 Month | 40° C./75% RH | 6 | 100.0 | Yes |
| 2 Months | 25° C./60% RH | 6 | 100.9 | Yes |
| 2 Months | 30° C./65% RH | 6 | 101.0 | Yes |
| 2 Months | 40° C./75% RH | 6 | 99.1 | Yes |
| 3 Months | 25° C./60% RH | 6 | 100.1 | Yes |
| 3 Months | 30° C./65% RH | 6 | 99.5 | Yes |
| 3 Months | 40° C./75% RH | 6 | 97.5 | Yes |
| 4 Months | 25° C./60% RH | 6 | 101.0 | Yes |
| 4 Months | 30° C./65% RH | 6 | 99.5 | Yes |
| 4 Months | 40° C./75% RH | 6 | 97.5 | Yes |
| 5 Months | 25° C./60% RH | 6 | 100.7 | Yes |
| 5 Months | 30° C./65% RH | 6 | 99.7 | Yes |
| 5 Months | 40° C./75% RH | 6 | 96.8 | Yes |

The data from Tables 9 and 10 are generally consistent with, and ultimately support the same conclusions in terms of stability as the results obtained from the batch reported in Tables 7 and 8.

Although these results can partially be attributed to minimizing the amount of inbound water in the tablets by including desiccant in the containers during packaging, or reducing atmospheric oxygen by purging the container prior to closure with an inert gas, the retention of nearly all of the levothyroxine sodium was completely unexpected.

It will be understood that the present description illustrates those aspects of the invention relevant to a clear understanding of the invention. Certain aspects that would be apparent to those of ordinary skill in the art and that, therefore, would not facilitate a better understanding of the invention have not been presented in order to simplify the present description. Although only a limited number of embodiments of the present invention are necessarily described herein, one of ordinary skill in the art will, upon considering the foregoing description, recognize that many modifications and variations of the invention may be employed. All such variations and modifications of the invention are intended to be covered by the foregoing description and the following claims.

What is claimed is:

1. A packaged immediate release oral solid dosage form product comprising:
    an immediate release oral solid dosage form including, by weight,
        about 0.1% to 1% levothyroxine salt,
        about 0.1% to about 8% HPMC, and
        about 0.01% to about 5% BHA; and
    a container closure system comprising a container of about 225 cm³ to about 360 cm³ and a sealing closure;
    provided that about 900 to about 1000 of the oral solid dosage forms and at least about 16 grams of desiccant are enclosed in the container and sealed with the sealing closure; and
    provided that each oral solid dosage form enclosed in the container retains at least 95% of an initial amount of the levothyroxine salt when stored at a temperature ranging from about 23° C. to about 27° C. and a relative humidity ranging from about 55% to about 65% for six months.

2. The packaged immediate release oral solid dosage form product of claim 1, wherein the container is purged with an inert gas prior to sealing with the sealing closure.

3. The packaged immediate release oral solid dosage form product of claim 2, wherein the inert gas comprises nitrogen.

4. The packaged immediate release oral solid dosage form product of claim 3, wherein the container is induction sealed with the sealing closure after the container is purged with the inert gas.

5. The packaged immediate release oral solid dosage form product of claim 1, provided that when the about 900 to about 1000 oral solid dosage forms and the at least about 6 grams of desiccant are placed in the container of about 225 cm³ to about 360 cm³ sealed with the sealing closure, each oral solid dosage form retains at least 95% of an initial amount of the levothyroxine salt when stored at a temperature ranging from about 38° C. to about 42° C. and a relative humidity ranging from about 70% to about 80% for three months.

6. A packaged immediate release oral solid dosage form product comprising:
    an immediate release oral solid dosage form including, by weight,
        about 0.1% to 1% levothyroxine salt and
        about 0.1% to about 8% HPMC; and
    a container closure system comprising a container of about 55 cm³ to about 125 cm³ and a sealing closure;

provided that about 90 to about 100 of the oral solid dosage forms and at least about 6 grams of desiccant are enclosed in the container and sealed with the sealing closure; and provided that each oral solid dosage form enclosed in the container retains at least 95% of an initial amount of the levothyroxine salt when stored at a temperature ranging from about 23° C. to about 27° C. and a relative humidity ranging from about 55% to about 65% for six months.

7. The packaged immediate release oral solid dosage form product of claim 6, wherein the container is purged with an inert gas prior to sealing with the sealing closure.

8. The packaged immediate release oral solid dosage form product of claim 7, wherein the inert gas comprises nitrogen.

9. The packaged immediate release oral solid dosage form product of claim 8, wherein the container is induction sealed with the sealing closure after the container is purged with the inert gas.

10. The packaged immediate release oral solid dosage form product of claim 6, provided that when the about 90 to about 100 oral solid dosage forms and the at least about 6 grams of desiccant are placed in the container of about 55 cm$^3$ to about 125 cm$^3$ sealed with the sealing closure, each oral solid dosage form retains at least 95% of an initial amount of the levothyroxine salt when stored at a temperature ranging from about 38° C. to about 42° C. and a relative humidity ranging from about 70% to about 80% for three months.

11. The packaged immediate release oral solid dosage form product of claim 6, wherein the immediate release oral solid dosage form further comprises a lubricant.

* * * * *